United States Patent [19]

Sebald

[11] Patent Number: 4,826,764

[45] Date of Patent: May 2, 1989

[54] ENHANCING THE TRANSLATIONAL INITIATION FREQUENCY OF A GENE

[75] Inventor: Walter Sebald, Wolfenbüttel, Fed. Rep. of Germany

[73] Assignee: Gesellschaft fur Biotechnologische Forschung mbH, Brunswick, Fed. Rep. of Germany

[21] Appl. No.: 756,136

[22] Filed: Jul. 17, 1985

[30] Foreign Application Priority Data

Jul. 18, 1984 [DE] Fed. Rep. of Germany ....... 3426532

[51] Int. Cl.⁴ ...................... C12P 21/00; C12P 19/34; C12N 7/00; C07H 15/12
[52] U.S. Cl. ........................................ 435/68; 435/70; 435/91; 435/172.3; 435/317.1; 435/252.33; 435/320; 536/27; 935/6; 935/29; 935/44; 935/73
[58] Field of Search ................... 435/68, 70, 243, 253, 435/172.3, 317, 320, 243; 536/27; 935/38, 44, 49, 6, 29, 73

[56] References Cited

PUBLICATIONS

Gray et al. (1981), Nucleic Acids Res. 9: 3919–26.
Bruislow et al. (1982), J. Bacteriology 151:1363–7.
Kastelein et al. (1983), Gene 23: 245–54.
McCarthy et al. (1984), *Abstract ed EBEC Mtg.*, Hannover.
Kastelein et al. (1983), Gene, vol. 23, pp. 245–254.

*Primary Examiner*—Thomas G. Wiseman
*Assistant Examiner*—S. Seidman
*Attorney, Agent, or Firm*—Kane, Dalsimer, Sullivan, Kurucz, Levy, Eisele and Richard

[57] ABSTRACT

The invention concerns the intercistronic DNA sequence of the atp operon of Escherichia coli for the subunit c of the ATP synthase, a DNA structure and an expression vector which are characterized by the said intercistronic DNA sequence, and a process for the production of proteins using the same. The DNA sequence enhances the rate of synthesis of the proteins.

16 Claims, No Drawings

ENHANCING THE TRANSLATIONAL INITIATION FREQUENCY OF A GENE

BACKGROUND OF THE INVENTION

1. Field of the Invention

The invention relates to a specific deoxyribonucleic acid sequence and the method of its use to improve yields of protein from expression of a gene within a microorganism.

2. Brief Description of the Prior Art

It is unclear which properties of mRNA make possible an optimum binding of ribosome and thus a maximum production of protein within the cell. A recent theory stresses the importance of the Shine-Dalgarno sequence (ribosome binding site), which must be placed at the correct distance from the start codon, and the importance of secondary structures of the mRNA which inhibit the start of the translation. There are, however, numerous indications that additional sequence elements of the mRNA are necessary for an effective formation of the initiation complex and thus an optimum translation. However, these sequence elements have not yet been identified.

It is known that the atp operon of *Escherichia coli* comprises 8 genes which code for the 8 subunits (a, c, b, delta, alpha, gamma, beta and epsilon) of the ATP synthase (adenosin triphosphate synthase). The atp operon is transcribed into a single polycistronic mRNA on which the subunits are translated or synthesized in different molar amounts. The highest translation rate can be observed for the subunit c.

SUMMARY OF THE INVENTION

The invention comprises the discovery that the intercistronic deoxyribonucleic acid (herein referred to at times as "DNA") sequence of the atp operon of *E. coli* for the sub-unit c of the ATP synthase functions to increase the expression of genes in *E. coli*.

DETAILED DESCRIPTION OF THE INVENTION

In the experiments on which the discovery was based the gene for the subunit c was isolated and cloned in expression vectors. It was found that the highest translation rate can be maintained only if a DNA sequence of about 40 base pairs in front of the Shine-Dalgarno sequence is present.

According to the invention high expression rates for structural genes in bacteria can be achieved if the following intercistronic DNA sequence derived from the *E. coli* atp operon is used.

| T | A | A |   |   |   |   |   |   |   |   |   |   |   |   |   | optional stop codon |
| A | T | T |   |   |   |   |   |   |   |   |   |   |   |   |   | for subunit a |
| T | T | T | A | C | C | A | A | C | A | C | T | A | C | T | A | C G T T intercistronic |
| A | A | A | T | G | G | T | T | G | T | G | A | T | G | A | T | G C A A sequence atp(a)-atp(c) |
| T | T | A | A | C | T | G | A | A | A | C | A | A | A | C | T |   |
| A | A | T | T | G | A | C | T | T | T | G | T | T | T | G | A |   |
| G | G | A | G |   |   |   |   |   |   |   |   |   |   |   |   | optional |
| C | C | T | C |   |   |   |   |   |   |   |   |   |   |   |   | Shine-Dalgarno sequence |
| A | C | T | G | T | C | A | T | G |   |   |   |   |   |   |   | optional start codon |
| T | G | A | C | A | G | T | A | C |   |   |   |   |   |   |   | for subunit c |

As shown in the chart above, the DNA sequence may include, optionally a stop codon belonging to the subunit a gene which precedes the subunit c gene in the operon.

The sequence may also include, optionally a Shine-Dalgarno sequence inserted immediately after the intercistronic sequence.

As also shown in the above chart, the sequence may include, optionally a start codon for the subunit c inserted immediately after the Shine-Dalgarno sequence or a DNA sequence is used the single strands of which can be hybridized (preferably at a temperature of at least 20° C. and especially at a concentration of 1M NaCl and a temperature of at least 25° C.) with those of the intercistronic sequence.

According to the invention a DNA structure with such a terminal DNA sequence inserted immediately in front of a given gene structure is also provided for this purpose.

According to the invention an expression vector is also provided which is characterized by presence of the above described DNA sequence.

EXAMPLE 1

The intercistronic DNA sequence atp(a)-atp(c) was recombined with cDNA for Interleukin-2 and after integration into an expression vector and transformation of *E. coli* it was found that the translation of this protein was drastically increased.

EXAMPLE 2

The intercistronic DNA sequence atp(a)-atp(c) was recombined with cDNA for β-interferon and after integration into an expression vector and transformation of *E. coli* an increased yield of β-interferon was achieved.

We claim:

1. A DNA molecule consisting of an intercistronic sequence of nucleotide base pairs having the formula:

TTTACCAACACTACTACGTTTTAACT-
    GAAACAAACT

AAATGGTTGTGATGATGCAAAATT-
    GACTTTGTTTGA.

2. A DNA construct comprising the DNA molecule of claim 1 adjacent to and immediately upstream of a structural gene other than the subunit c of the ATP synthase operon.

3. An expression vector containing the DNA construct of claim 2 such that the structural gene is expressible.

4. A method of enhancing the expression of a structural gene in *E. coli* comprising transforming *E. coli* host cells with the vector of claim 3 and culturing the cells under conditions in which the protein encoded by the structural gene is expressed.

5. The method of claim 4 wherein the structural gene encodes interleukin-2.

6. The method of claim 4 wherein the structural gene encodes beta-interferon.

7. The DNA construct of claim 2 containing a stop codon adjacent to and immediately upstream of the intercistronic sequence.

8. The DNA construct of claim 7 containing a Shine-Dalgarno sequence adjacent to and immediately downstream of the intercistronic sequence.

9. The DNA construct of claim 8 wherein DNA having the nucleotide sequence

ACTGTCATG

TCACAGTAC is inserted adjacent to and immediately downstream of the Shine-Dalgarno sequence.

10. The DNA molecule consisting of about 40 nucleotide base pairs that is capable of effecting enhanced protein expression and hybridizing in 1M NaCl at a temperature of at least 25° C. to the intercistronic sequence.

11. A DNA construct comprising the DNA molecule of claim 10 adjacent to and immediately upstream of a structural gene other than the subunit c of the ATP synthase operon.

12. An expression vector containing the DNA construct of claim 11 in a manner such that the structural gene is expressed.

13. A method of enhancing the expression of a structural gene in *E. coli* comprising transforming *E. coli* host cells with the vector of claim 12 and culturing the cells under conditions in which the protein encoded by the structural gene is expressed.

14. An expression vector containing the DNA construct of claim 11 such that the structural gene is expressible.

15. The DNA construct of claim 11 containing a stop codon adjacent to and immediately upstream of the DNA molecule consisting of about 40 nucleotides that is capable of effecting enhanced expression and hybridizing in 1M NaCl at a temperature of at least 25 C. to the intercistronic sequence.

16. The DNA construct of claim 15 containing a Shine-Dalgarno sequence adjacent to and immediately downstream of the DNA molecule consisting of about 40 nucleotides that is capable of effecting enhanced expression and hybridizing in 1M NaCl at a temperature of at least 25 C. to the intercistronic sequence.

* * * * *